US007019195B1

(12) United States Patent
Heifetz et al.

(10) Patent No.: US 7,019,195 B1
(45) Date of Patent: Mar. 28, 2006

(54) METHOD FOR CONFERRING RESISTANCE OR TOLERANCE AGANIST FUROVIRUS, POTYVIRUS, TOSPOVIRUS, AND CUCOMOVIRUS TO PLANT CELLS

(75) Inventors: Peter Bernard Heifetz, Durham, NC (US); David Andrew Patton, Durham, NC (US); Joshua Zvi Levin, Durham, NC (US); Qiudeng Que, Apex, NC (US); Petrus Theodorus De Haan, Enkhuizen (NL); Johannes Jacobus Ludgerus Gielen, Aucamville (FR)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/309,038

(22) Filed: May 10, 1999

Related U.S. Application Data

(60) Provisional application No. 60/150,705, filed on May 26, 1998.

(51) Int. Cl.
  *C12N 15/82*  (2006.01)
  *C12N 15/90*  (2006.01)
  *C12N 5/10*  (2006.01)
  *A01H 5/00*  (2006.01)

(52) U.S. Cl. .................. 800/280; 800/286; 800/287; 800/301; 435/419; 435/468

(58) Field of Classification Search ............... 435/69.1, 435/320.1, 410, 419, 468, 455, 471; 800/278, 800/279, 280, 285, 286, 287, 21, 288
See application file for complete search history.

(56) References Cited

U.S. PATENT DOCUMENTS

| | | | |
|---|---|---|---|
| 5,738,985 A * | 4/1998 | Miles et al. .................. 435/5 |
| 5,907,084 A | 5/1999 | de Haan ..................... 800/279 |
| 5,939,600 A | 8/1999 | Goldbach et al. ........... 800/278 |
| 6,506,559 B1 * | 1/2003 | Fire et al. ..................... 435/6 |

FOREIGN PATENT DOCUMENTS

| | | |
|---|---|---|
| EP | 0 426 195 A1 | 8/1991 |
| EP | 0458367 A | 11/1991 |
| WO | 9417176 | 8/1994 |
| WO | WO 95/09920 | 4/1995 |
| WO | 9932619 | 12/1998 |
| WO | 9915682 | 4/1999 |
| WO | 9953050 | 4/1999 |

OTHER PUBLICATIONS

Stam et al, The Silence of Genesin Transgenic Plants, 1997, Annals of Botany 79: pp. 3-12.*
Krueger et al, "A Brown Algal Virus Genome contains a "Ring" Zince Finger Motif", 1996, Virology 219 pp. 301-303.*
Olivier Voinnet et al., Suppression of gene silencing: A general strategy used by diverse DNA and RNA viruses of plants, PNAS, vol. 96, No. 24, Nov. 23, 1999, pp. 14147-14152.*
Mary K. Montgomery et al., Double-stranded RNA as a mediator in sequence-specific genetic silencing and co-suppression. TIG, vol. 14, No. 7, Jul. 1998, pp. 255-257.*
Andrew Fire et al., Potent and specific genetic interference by double-stranded RNA in Caenorhabditis elegans, NATURE, vol. 391, Feb. 1998, pp. 806-811.*
James S. Keddie et al., A seed-specific Brassica napus oleosin promoter interacts with a G-box-specific protein and may be bi-directional, Plant Molecular Biology, 24, pp. 327-340.*
McManus et al., Keystone Symposia, Taos, New Mexico, Feb. 21-26, 2002, Abstract No. 214.*
Pachuk et al., Keystone Symposia, Taos, New Mexico, Feb. 21-26, 2002, Abstract No. 217.*
Cabello et al., Keystone Symposia, Taos, New Mexico, Feb. 21-26, 2002, Abstract No. 303.*
Hadwiger et al., Keystone Symposia, Taos, New Mexico, Feb. 21-26, 2002, Abstract No. 310.*
Lewis et al., Keystone Symposia, Taos, New Mexico, Feb. 21-26, 2002, Abstract No. 312.*
Gelck et al., Keystone Symposia, Taos, New Mexico, Feb. 21-26, 2002, Abstract No. 307.*
Elbashir et al., Keystone Symposia, Toas, New Mexico, Feb. 21-26, 2002, Abstract No. 306.*
Paddison et al., Proc. Natl. Acad. Sci., USA, 2002, vol. 99, pp. 1443-1448.*
Elbashir et al., Nature, 2001, vol. 411, pp. 494-498.*
Wianny et al., Nature Cell Biol., 2000, vol. 2, pp. 70-75.*
Svoboda et al., Development, 2000, vol. 127, pp. 4147-4156.*
Bahramian et al., Mol. Cell. Biol., 1999, vol. 19, pp. 274-283.*
Oates et al., Dev. Biol., 2000, vol. 224, pp. 20-28.*
Voinnet, O., Trends in Genetics, 2001, vol. 17 , pp. 449-459.*
Peele et al. , Plant J., 2001, vol. 27, pp. 357-366.*
de Haan et al., J. Gen. Virol., 1991, vol. 71, pp. 2207-2216.*

(Continued)

*Primary Examiner*—Ashwin Mehta
(74) *Attorney, Agent, or Firm*—Mary Kakefuda

(57) ABSTRACT

The present invention relates to a method to confer resistance or tolerance to more than one virus from the group consisting of furovirus, potyvirus, tospovirus, and cucomovirus, using sense and antisense RNA fragments of a sequence from their genomes. The sense and antisense RNA fragments are capable of pairing and forming a double-stranded RNA molecule, thereby reducing expression of the viral genome.

35 Claims, No Drawings

OTHER PUBLICATIONS

Maiss et al., J. Gen. Virol., 1989, vol. 70, pp. 513-524.*
Saito et al., Arch. Virol., 1996, vol. 141, pp. 2163-2175.*
Hsu et al., Arch. Virol., 1995, vol. 140, pp. 1841-1847.*
Miki et al., Procedures for Introducing Foreign DNA into Plants, In Methods in Plant Molecular Biology and Biotechnology, 1993, Bernard R. Glick and John E. Thompson, Eds., CRC Press, Inc., Boca Raton, FL.*
Bouzoubaa et al., J. Gen. Virol., 1987, vol. 68, pp. 615-626.*
Baulcombe, D.C., Plant Cell, 1996, vol. 8, pp. 1833-1844.*
CRC Handbook on Diseases of Sugar Beet, "Virus Yellows," vol. 2: pp. 35-52 (1998).
Fire, A et al., "Potent and specific genetic interference by double-stranded RNA in Caenorhabditis elegans," Nature, 391: pp. 803-811 (1998).
Hamilton, A.J. et al., "A Transgene with repeated DNA causes high frequency, post-transcriptional suppression of ACC-oxidase gene expression in tomato," Plant Journal, 15(6): pp. 737-746 (1998).
Martelli, G.P., "Classification and Nomenclature of Plant Viruses: State of the Art," Plant Disease, 76(5): pp. 436-442 (1992).
Matzke, M.A.. & Matzke, A.J.M., "How and Why Do Plants Inactivate Homologus (Trans)genes?" Plant Physiol., 107: pp. 679-685 (1995).

Ratcliff, F. et al., "A Similarity Between Viral Defense and Gene Silencing in Plants," Science, 276: pp. 1158-1560 (1997).
Rush, C.M. and Heidel, G.B., "Furovirus Diseases of Sugar Beets in the United States," Plant Disease, 79(9): pp. 868-875 (1995).
Sijen, T. et al., "RNA-Mediated Virus Resistance: Role of Repeated Transgenes and Delineation of Targeted Regions," Plant Cell, 8: pp. 2277-2294 (1996).
Waterhouse, P.M. et al., "Virus resistance and gene silencing in plants can be induced by simultaneous expression of sense and antisense RNA," Proc. Natl. Acad. Sci. USA, 95: pp. 13959-13964 (1998).
Zaccomer, B. et al., "The remarkable variety of plant RNA virus genomes," Journal of General Virology, 76: pp. 231-247 (1995).
Dale et al., Intra—and intermolecular site-specific recombination in plant cells mediated by bacteriophage P1 recombinase, GENE, 91:79-85, 1990.
Wassenegger, M. & Pelissier, T., A model for RNA-mediated gene silencing in higher plants, Plant Molecular Biology, 37:349-362, May 1998.
Stam et al., Post-transcriptional silencing of chalcone.

* cited by examiner

METHOD FOR CONFERRING RESISTANCE OR TOLERANCE AGANIST FUROVIRUS, POTYVIRUS, TOSPOVIRUS, AND CUCOMOVIRUS TO PLANT CELLS

This application claims the benefit of U.S. Provisional Application No. 60/150,705, which was converted on May 10, 1999, from application Ser. No. 09/084,942, filed May 26, 1998. The disclosure of which is hereby expressly incorporated by reference in its entirety into the instant disclosure.

FIELD OF THE INVENTION

The present invention relates to methods of altering the expression of genes in cells, plants or animals, in particular using sense and antisense RNA fragments of said genes, and to cells, plants or animals with altered gene expression obtained using the methods of the present invention. The invention particularly relates to such cells, plants or animals resistant or tolerant to viruses.

BACKGROUND OF THE INVENTION

Developments in the techniques of molecular biology and transformation have allowed the production of transgenic cells, plants or animals with various desirable traits, such as, e.g., resistance to insects and diseases, such fungal or microbial pathogens, tolerance to herbicides or value-added traits. These desirable traits are mainly obtained by overexpression of a transgene in the cells, plants or animals. However, in some cases, it is also desirable to modify cells, plants or animals so that the expression of a particular gene is altered to create cells, plants or animals with desirable phenotypes or properties of commercial interest. Current methods to alter the expression of a gene usually rely upon techniques of sense (see e.g. Jorgensen et al. (1996) Plant Mol. Biol. 31: 957–973) or antisense suppression (see e.g. Green, P. J. et al. (1986) Ann. Rev. Biochem. 55:569–597). For example, sense suppression of a chalcone synthase gene in Petunia results in flowers with altered pigmentation and antisense suppression of a polygalacturonidase gene in tomato leads to delayed fruit ripening. Unfortunately, these methods are often variable and unpredictable in their ability to alter gene expression, and in many cases a complete disruption of the particular gene activity is not achieved. Other methods to alter gene expression include the use of catalytic ribonucleotides or ribozymes (see e.g. U.S. Pat. No. 4,987,071), which can be technically challenging, or homologous gene disruption (see e.g. Paszkowski et al. (1988) EMBO Journal 7: 4021–4026), which although the most desirable genetically, is unfortunately often not efficient enough with currently available techniques to be routinely used for such purposes.

Another area of deep interest is resistance or tolerance to viruses. Viruses affect most living organisms. In crops, large proportions of the harvest may be lost due to virus infections. Farm animals are also often infected by viruses and must sometimes be slaughtered to prevent spreading of the disease leading to dramatic economic consequences. Companoin animals are also affected by viruses, and, finally, viruses infect humans causing a lot of suffering. Although treatments against viruses have been developed, they are very often either extremely expensive or of limited efficiency.

There is therefore a long-felt but unfulfilled need for novel methods and compositions allowing one to effectively and predictably alter the expression of a gene to obtain cells, plants or animals with improved and commercially important properties. In particular there is a long-felt but unfulfilled need for such methods that provide resistance or tolerance to viruses.

SUMMARY OF THE INVENTION

The present invention relates to the production of cells, plants or animals with improved properties and traits using molecular techniques and genetic transformation. In particular, the invention relates to methods of altering the expression of a gene in cells, plants or animals using sense and antisense RNA fragments of the gene. Importantly, such sense and antisense RNA fragments are capable of forming a double-stranded RNA molecule. Particularly, the present invention relates to methods and compositions of conferring upon a cell, plant or animal resistance or tolerance to viruses. Preferably the invention relates to methods of conferring upon a plant resistance or tolerance to viruses. The invention also preferably relates to plant cells obtained using such methods, to plants derived from such cells, to the progeny of such plants and to seeds derived from such plants. In such plant cells or plants, the alteration of the gene expression of a particular gene is more effective, selective and more predictable than the alteration of the gene expression of a particular gene obtained using current methods known in the art.

The invention therefore provides:

A method comprising introducing into a cell a plurality of sub-sequences, e.g. RNA fragments or DNA sequences, characterized in that at least two of the sub-sequences have sense and antisense sequences of viral RNAs and are capable of forming a double-stranded RNA molecule. Preferably, the method comprises introducing into a cell an RNA which consists of a plurality of sub-sequences characterized in that at least two of the sub-sequences have the sequences of viral RNAs. Preferably, the RNA contains at least one translational stop codon located upstream of the 3' terminal sub-sequence. In another preferred embodiment, the method comprises introducing into a cell a nucleotide sequence or DNA molecule encoding said RNA.

The invention therefore provides:

A method comprising introducing into a cell a sense RNA fragment of a target gene and an antisense RNA fragment of said target gene, wherein said sense RNA fragment and said antisense RNA fragment are capable of forming a double-stranded RNA molecule, wherein the expression of said target gene in said cell is altered. In a preferred embodiment, the target gene comprises a viral genome or a portion thereof and the cell is preferably resistant or tolerant to viruses. In a preferred embodiment, the virus is selected from the group consisting of topsoviruses, potyviruses, potexviruses, tobamoviruses, luteoviruses, cucumoviruses, bromoviruses, closteorviruses, tombusviruses and furoviruses. In another preferred embodiment, the RNA fragments comprises a nucleotide sequence derived from a viral coat protein gene, a viral nucleocapsid protein gene, a viral replicase gene, a movement protein gene or portions thereof. In a further preferred embodiment, a cell is a plant cell, such as a monocotyledonous or a dicotyledonous cell. In another preferred embodiment, the RNA fragments are comprised in two different RNA molecules. In another preferred embodiment, the RNA fragments are mixed before being introduced into said cell. In another preferred embodiment, the RNA fragments are mixed before being introduced into said cell under conditions allowing them to form a double-stranded RNA molecule. In another preferred embodiment, the RNA fragments are introduced into said cell sequentially. In yet another preferred embodiment, the RNA fragments are comprised in one RNA molecule. In such case, the RNA molecule is preferably capable of folding such that said RNA fragments comprised therein form a double-stranded RNA molecule.

The invention further provides:

A method comprising introducing into a cell a first DNA sequence capable of expressing in said cell a sense RNA fragment of a target gene, and a second DNA sequence capable of expressing in said cell an antisense RNA fragment of said target gene, wherein said sense RNA fragment and said antisense RNA fragment are capable of forming a double-stranded RNA molecule, wherein the expression of said target gene in said cell is altered. In a preferred embodiment, the target gene comprises a viral genome or a portion thereof and the cell is preferably resistant or tolerant to viruses. In a preferred embodiment, the virus is selected from the group consisting of topsoviruses, potyviruses, potexviruses, tobamoviruses, luteoviruses, cucumoviruses, bromoviruses, closteorviruses, tombusviruses and furoviruses. In another preferred embodiment, the DNA sequences comprises a nucleotide sequence derived from a viral coat protein gene, a viral nucleocapsid protein gene, a viral replicase gene, a movement protein gene or portions thereof. In a further preferred embodiment, a cell is a plant cell, such as a monocotyledonous or a dicotyledonous cell. In a preferred embodiment, the DNA sequences are stably integrated in the genome of the plant cell. In a preferred embodiment, the DNA molecule further comprises a promoter operably linked to said first or said second DNA sequence. In another preferred embodiment, the first DNA sequence and the second DNA sequence are comprised in two different DNA molecules.

Alternatively, the first DNA sequence and the second DNA sequence are comprised in one DNA molecule. In this case, the first DNA sequence and the second DNA sequence are preferably comprised in the same DNA strand of said DNA molecule, and, preferably, the sense RNA fragment and the antisense RNA fragment are comprised in one RNA molecule. Preferably, the RNA molecule is capable of folding such that said RNA fragments comprised therein form a double-stranded region. In another preferred embodiment, the sense RNA fragment and the antisense RNA fragment are comprised in two RNA molecules. In this case, the first DNA sequence and the second DNA sequence are preferably operably linked to a bi-directional promoter or, alternatively, the first DNA sequence is operably linked to a first promoter and the second DNA sequence is operably linked to a second promoter, wherein the first promoter and the second promoter comprise the same promoter or comprise different promoters. In another preferred embodiment, the first DNA sequence and the second DNA sequence are comprised in complementary strands of said DNA molecule.

In yet another preferred embodiment, the first DNA sequence is the complementary DNA strand of the second DNA sequence in said DNA molecule. In this case, the DNA molecule further comprises a first promoter operably linked to said first or second DNA sequence. In a preferred embodiment, the DNA molecule further comprises a first site-specific recombination site between said first promoter and said first or second DNA sequence and a second site-specific recombination site at the 3'end of said first DNA sequence, wherein said first and second site-specific recombination sites are capable of inverting said first or second DNA sequence between said first and second site-specific recombination sites in presence of a site-specific recombinase. In a further preferred embodiment and as a result of said inverting said first promoter is capable of expressing said second (or first, depending on which DNA sequence was originally linked to the promoter) DNA sequence. The plant cell preferably further comprises a site-specific recombinase capable of recognizing said site-specific recombination sites.

In yet another preferred embodiment, the DNA molecule further comprises a first promoter operably linked to said first DNA sequence and a second promoter operably linked to said second DNA sequence, wherein the first promoter and the second promoter comprise the same promoter or comprise different promoters.

In another preferred embodiment, the promoter in the DNA molecule comprises a native promoter of said cell. In a further preferred embodiment, the promoter is a heterologous promoter, for example a tissue specific promoter, a developmentally regulated promoter, a constitutive promoter or an inducible promoter. Optionally, the promoter is a divergent promoter capable of initiating transcription of DNA sequences on each side of the promoter.

In yet another preferred embodiment, the DNA sequence further comprises a linker between the DNA sequences encoding said the sense and antisense RNA fragments. The linker comprises, e.g. an expression cassette comprising a functional gene, e.g. a selectable marker gene or regulatory sequences, e.g. intron processing signals.

The invention also further provides:

A cell comprising the sense and antisense RNA fragments of the present invention, wherein the expression of said target gene in said cell is altered by said RNA fragments. In a preferred embodiment, the cell is resistant or tolerant to viruses. In a preferred embodiment, the cell is a plant cell and the invention further provides a plant and the progeny thereof derived from the plant cell, and seeds derived from the plant.

The invention also further provides:

A cell obtained by a method of the present invention. In a preferred embodiment, the cell is a plant cell.

The invention also provides:

DNA constructs comprising the DNA sequences of the present invention.

In a preferred embodiment, such a DNA construct comprises a first DNA sequence capable of expressing in a cell a sense RNA fragment of a viral genome or portion thereof and a second DNA sequence capable of expressing in said cell an antisense RNA fragment of said viral genome or portion thereof, wherein said sense RNA fragment and said antisense RNA fragment are capable of forming a double-stranded RNA molecule. In another preferred embodiment, the expression of said viral genome or portion thereof in said cell is altered. In another preferred embodiment, the cell is a plant cell. In another preferred embodiment, the virus is selected from the group consisting of topsoviruses, potyviruses, potexviruses, tobamoviruses, luteoviruses, cucumoviruses, bromoviruses, closteorviruses, tombusviruses and furoviruses. In another preferred embodiment, the DNA sequences comprises a nucleotide sequence derived from a viral coat protein gene, a viral nucleocapsid protein gene, a viral replicase gene, a movement protein gene or portions thereof. In yet another preferred embodiment, the DNA construct further comprises a promoter operably linked to said first or said second DNA sequence. In yet another preferred embodiment, the DNA construct further comprises a first promoter operably linked to said first DNA sequence and a second promoter operably linked to said second DNA sequence. In yet another preferred embodiment, the DNA construct further comprises a bi-directional promoter operably linked to said first DNA sequence and said second DNA sequence.

The invention further provides:

A DNA construct comprises a first DNA sequence capable of expressing in a cell a sense RNA fragment of a target gene and a second DNA sequence capable of expressing in said cell an antisense RNA fragment of said target gene, wherein said sense RNA fragment and said antisense RNA fragment are capable of forming a double-stranded RNA molecule, wherein said DNA construct further comprises a bi-directional promoter operably linked to said first DNA sequence and to said second DNA sequence. In another preferred embodiment, the expression of said target gene in said cell is altered.

The invention further provides:

A DNA construct comprising:
- (a) a first DNA sequence capable of expressing in a cell a sense RNA fragment of a target gene and a second DNA sequence capable of expressing in said cell an antisense RNA fragment of said target gene, wherein said sense RNA fragment and said antisense RNA fragment are capable of forming a double-stranded RNA molecule, wherein said first DNA sequence is the complementary strands of said second DNA sequence in said DNA construct,
- (b) a promoter operably linked to said first or second DNA sequence,
- (c) a first site-specific recombination site between said promoter and said first or second DNA sequence, and
- (d) a second site-specific recombination site at the 3'end of said first or second DNA sequence, wherein said first and second site-specific recombination sites are capable of inverting said first or second DNA sequence between said first and second site-specific recombination sites in presence of a site-specific recombinase.

In a preferred embodiment, the expression of said target gene in said cell is altered.

The invention further provides:

A DNA construct comprising:
- (a) a first DNA sequence capable of expressing in a cell a sense RNA fragment of a target gene and a second DNA sequence capable of expressing in said cell an antisense RNA fragment of said target gene, wherein said sense RNA fragment and said antisense RNA fragment are capable of forming a double-stranded RNA molecule, wherein said first DNA sequence is the complementary strands of said second DNA sequence in said DNA construct,
- (b) a first promoter operably linked to said first DNA sequence,
- (c) a second promoter operably linked to said second DNA sequence.

In a preferred embodiment, the expression of said target gene in said cell is altered.

The invention further provides:

A recombinant vector comprising a DNA construct of the present invention.

The invention also provides:

A composition comprising a DNA construct of the present invention.

DEFINITIONS

A "double-stranded RNA (dsRNA)" molecule comprises a sense RNA fragment of a target gene and an antisense RNA fragment of the same target gene, which both comprise nucleotide sequences complementary to one another, thereby allowing the sense and antisense RNA fragments to pair and form a double-stranded RNA molecule.

"Complementary" refers to two nucleotide sequences which comprise antiparallel nucleotide sequences capable of pairing with one another upon formation of hydrogen bonds between the complementary base residues in the antiparallel nucleotide sequences.

"Antiparallel" refers herein to two nucleotide sequences paired through hydrogen bonds between complementary base residues with phosphodiester bonds running in the 5'–3' direction in one nucleotide sequence and in the 3'–5' direction in the other nucleotide sequence.

A "target gene" is any gene of a cell. A target gene is a gene of known function or is a gene whose function is unknown, but whose total or partial nucleotide sequence is known. A target gene is an native gene of the cell or is a heterologous gene which had previously been introduced into the cell, preferably by genetic transformation of the cell. Preferably, the target gene is a gene in a plant cell.

A "native" refers to a gene which is present in the genome of the untransformed cell.

An "essential" gene is a gene encoding a protein such as e.g. a biosynthetic enzyme, receptor, signal transduction protein, structural gene product, or transport protein that is essential to the growth or survival of the cell.

To "alter" the expression of a target gene in cell means that the level of expression of the target gene in cell after applying a method of the present invention is different from its expression in the cell before applying the method. To alter gene expression preferably means that the expression of the target gene in the cell is reduced, preferably strongly reduced, more preferably the expression of the gene is not detectable, resulting in a knockout mutant phenotype in cells or plants or animals derived thereof.

"Isolated" is, in the context of the present invention, an isolated nucleic acid molecule that, by the hand of man, exists apart from its native environment and is therefore not a product of nature. An isolated nucleic acid molecule may exist in a purified form or may exist in a non-native environment such as, for example, a transgenic host cell.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue or organ or stage of development.

"Heterologous" as used herein means "of different natural origin" or represents a non-natural state. For example, if a host cell is transformed with a nucleic acid sequence derived from another organism, particularly from another species, that nucleic acid sequence is heterologous with respect to that host cell and also with respect to descendants of the host cell which carry that nucleic acid sequence. Similarly, heterologous refers to a nucleotide sequence derived from and inserted into the same natural, original cell type, but which is present in a non-natural state, e.g. a different copy number, or under the control of different regulatory elements.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence (number of complementary bases in the complementary sequence divided by total number of bases in the complementary sequence) desirably is at least 80%, more desirably 85%, preferably at least 90%, more preferably at least 95%, still more preferably at least 99%.

"Regulatory elements" refer to sequences involved in conferring the expression of a nucleotide sequence. Regulatory elements comprise a promoter operably linked to the nucleotide sequence of interest and termination signals. They also typically encompass sequences required for proper translation of the nucleotide sequence.

A "plant" refers to any plant or part of a plant at any stage of development. Therein are also included cuttings, cell or tissue cultures and seeds. As used in conjunction with the present invention, the term "plant tissue" includes, but is not limited to, whole plants, plant cells, plant organs, plant seeds, protoplasts, callus, cell cultures, and any groups of plant cells organized into structural and/or functional units.

"Virus resistance or tolerance" means herein that a resistant or tolerant cell, plant or animal is not susceptible to one or more viruses or has reduced susceptibility to one or more viruses as compared to a sensitive cell, plant or animal. Resistance or tolerance means for example that the usual symptoms of a virus infection are reduced or absent, or that accumulation or replication of the virus in the cell is reduced or prevented, or that movement of the virus, e.g. from cell to cell is reduced or prevented.

By "alteration of the expression of the viral genome or of a portion thereof" is typically understood that accumulation, replication or movement of the virus or a portion thereof, e.g. a RNA, DNA or protein portion of the virus, in the cell is affected.

DETAILED DESCRIPTION OF THE INVENTION

The present invention relates to methods to regulate the expression of a gene in cells, plants or animals. Commonly available methods to regulate the expression of a gene in cells, plants or animalslack predictability and show variability depending upon which gene is to be regulated. The present method alleviates these problems and provides for reproducible and efficacious regulation of a gene in cells, plants or animals.

Preferably, the gene the expression of which is regulated is a viral genome or a portion thereof. In a preferred embodiment, a cell is an eukaryotic cell, more preferably a plant cell, such as a monocotyledonous or a dicotyledonous cell, or an animal cell e.g. from a mammal, e.g. a human, a bovine, an ovine, a porcine, a feline or a canine, or from an avian.

The present invention utilizes a sense RNA fragment and an antisense RNA fragment of a target gene to alter the expression of the gene in a cell. In a first embodiment, the invention provides method comprising introducing into a cell a sense RNA fragment of a target gene and an antisense RNA fragment of said target gene, wherein said sense RNA fragment and said antisense RNA fragment are capable of forming a double-stranded RNA molecule, wherein the expression of said target gene in said cell is altered. The RNA fragments are introduced in the cells by different transformation methods. For example, the RNA fragments are transferred to the host cells using particle bombardment as described in co-pending application Ser. No. 08/717,676, issued on Apr. 18, 2000 as U.S. Pat. No. 6,051,409. In another preferred embodiment, the RNA fragments are introduced into the protoplasts or other types of cells by PEG-mediated transformation as described in Lebel et al. (1995) Theor. Appl. Genet. 91: 899–906 or by electroporation. In another preferred embodiment, other techniques, such as microinjection of the RNA fragments, are used.

In a preferred embodiment, the RNA fragments are comprised in two different RNA molecules. In this case, the RNA fragments are mixed before being introduced into said cell, e.g. under conditions allowing them to form a double-stranded RNA molecule. In another preferred embodiment, the RNA fragments are introduced into said cell sequentially. Preferably, the time interval between the introduction of each of the RNA molecules is short, preferably less than one hour. In yet another embodiment, the RNA fragments are comprised in one RNA molecule. By using one single RNA molecule the two complementary RNA fragments are in close proximity such that pairing and is favored. In such case, the RNA molecule is preferably capable of folding such that said RNA fragments comprised therein form a double-stranded region. In this case, the complementary parts of the RNA fragments recognize one another, pair with each other and form the double-stranded RNA molecule. In a preferred embodiment, the RNA fragments are incubated under conditions allowing them to form a double-stranded RNA molecule prior to introduction into the cell. In yet another embodiment, the RNA molecule comprises a linker between the sense RNA fragment and the antisense RNA fragment. The linker preferably comprises a RNA sequence encoded by an expression cassette comprising a functional gene, e.g. a selectable marker gene. In another embodiment, the linker comprises a RNA sequence encoded by regulatory sequences, which e.g. comprise intron processing signals.

In a further embodiment, the present invention provides a method comprising introducing into a cell a first DNA sequence capable of expressing in said cell a sense RNA fragment of a target gene and a second DNA sequence capable of expressing in said cell an antisense RNA fragment of said target gene, wherein said sense RNA fragment and said antisense RNA fragment are capable of forming a double-stranded RNA molecule, wherein the expression of said target gene in said cell is altered. In a preferred embodiment, the first DNA sequence and the second DNA sequence are stably integrated in the genome of the cell. In another preferred embodiment, the DNA sequences are comprised in two different DNA molecules. In another preferred embodiment, the DNA sequences are comprised in one DNA molecule. In such case, the DNA molecule preferably encodes a single RNA molecule which comprises the sense and antisense RNA fragments. By using one single RNA molecule the two complementary RNA fragments are in close proximity such that pairing and is favored. The DNA molecule encodes two separate RNA molecules, e.g. one RNA molecule comprising a sense RNA fragment and one RNA molecule comprising an antisense RNA fragment. The single RNA molecule or the two distinct RNA molecules are preferably capable of folding such that said RNA fragments comprised therein form a double-stranded region, in which the complementary parts of the RNA fragments recognize one another, pair with each other and form the double-stranded RNA molecule.

In a preferred embodiment, the single DNA molecule or each of the two distinct DNA molecules further comprises a promoter operably linked to said DNA sequences. In a preferred embodiment, a promoter in the DNA sequence comprises an native promoter of said native gene to be inactivated, in order to insure that the double-stranded RNA is present in the same tissues and at the same time in development as is the target gene is expressed. In another embodiment the promoter is a heterologous promoter, for example a tissue specific promoter, a developmentally regulated promoter, a constitutive promoter or an inducible promoter. In another embodiment the gene is an heterologous gene in said cell.

In yet another embodiment, the DNA sequence further comprises a linker between the DNA sequences encoding said two complementary RNA fragments. The linker preferably comprises an expression cassette comprising a functional gene, e.g. a selectable marker gene. In another embodiment, the linker comprises regulatory sequences, which e.g. comprise intron processing signals.

DNA molecules of the present invention are transformed into cells using methods well-known in the art or described below. The present invention also comprises a DNA construct comprising DNA sequences of the present invention, a recombinant vector comprising such DNA constructs and a composition comprising DNA sequences of the present invention.

In the present invention the length of the complementary region between the sense and antisense RNA fragments comprises desirably at least 15 nucleotides long, more desirably at least 50 nucleotides long, preferably at least 500 bp long. Preferably, the complementary region is less than 5 kb, more preferably less than 2 kb. Preferably, the complementary region between the sense and antisense RNA fragments comprises the coding region of the target gene. In other preferred embodiment, the complementary region comprises untranslated regions (UTR) of the target gene, e.g. 5' UTR or 3' UTR. In another preferred embodiment, a DNA sequence encoding a sense or antisense RNA fragment of the present invention is derived from a c-DNA molecule. In another embodiment, the complementary sequences comprise regulatory elements of the target gene whose expression is altered, such as promoter or termination signals.

In another preferred embodiment, the complementary region between the sense and antisense RNA fragments is identical to the corresponding sequence of the gene whose expression is altered. In another preferred embodiment, the complementary region between the sense and antisense RNA fragments is substantially similar to the corresponding sequence of the gene whose expression is altered and is still capable of altering the expression of the gene. In this case, the complementary region is desirably at least 50% identical to the corresponding sequence of the gene whose expression is altered more desirably at least 70% identical, preferably at least 90% identical, more preferably at least 95% identical. Thereby, using a single double-stranded RNA molecule allows to alter the expression of a single gene or of a plurality of genes, the single gene comprising sequences identical to the double-stranded RNA or being substantially similar to the double-stranded RNA.

In another preferred embodiment, the complementary region between the sense and antisense RNA fragments does not contain any mismatch between the sense and antisense RNA fragments. In another preferred embodiment, the complementary region between the sense and antisense RNA fragments comprises at least one mismatch between the sense and antisense RNA fragments, and the two RNA fragments are still capable of pairing and forming a double-stranded RNA molecule, thereby altering the expression of the gene. Desirably, there is less than 50% mismatch between the sense and antisense RNA fragments in the complementary region, more desirably less than 30% mismatch, preferably less than 20% mismatch, more preferably less than 10% mismatch, yet more preferably less than 5% mismatch.

A method of the present invention is used for example to alter the expression of a gene involved in a metabolic pathway of a plant cell, in resistance or susceptibility of a plant to diseases or in cell differentiation, Such alterations result in plants with commercially important improved traits, such as modifications of the particular metabolic pathway, resistance to diseases or changes in cell differentiation. Other examples of target genes are described e.g. in U.S. Pat. Nos. 5,107,065, 5,283,184 and 5,034,323, herein incorporated by reference. A method of the present invention is also used to alter the expression of a gene in order to unravel its function. In this case, for example, DNA sequences capable of expressing sense and antisense RNA fragments of the gene are introduced into a plant cell by a transformation method well known in the art or described below. The DNA sequences are for example stably integrated in the genome of the plant cell. The plant cell is then examined for e.g. phenotypic or metabolic changes. Alternatively, a plant is regenerated from the plant cell and the plant or its progeny is examined for, e.g., phenotypic or metabolic changes. For example, essential genes are discovered using such a method and screening the transformed plants for e.g. embryo lethality, seedling lethality or other relevant phenotypes. Knowledge of the function of the gene is then used to produce crops with improved properties by genetic transformation or to screen for novel chemicals. In particular, essential genes are good candidates as targets for herbicidal compounds. Essential gene sequences, are for example overexpressed in a plant to confer resistance upon the plant to a herbicidal compound which inhibit the function of the naturally occurring enzyme encoded by the gene. Mutated variants of the essential gene are also produced and screened for tolerance to the herbicidal compound or to related compounds. Such mutated variants are produced by various methods known in the art. The enzyme encoded by the essential gene is also used to screen for compounds which inhibit its function, e.g. in a in-vitro high throughput screen. Inhibiting compounds are then tested for herbicidal activity.

A method of the present invention is also used to randomly alter the expression of genes without prior knowledge of their nucleotide sequence. In this case, a library of random RNA fragments capable of pairing and forming double-stranded RNA molecules or a library of random DNA sequences encoding RNA fragments capable of pairing and forming a double-stranded RNA molecule is prepared and introduced into plant cells using methods well-known in the art or described below. The transformed plant cells or plants are screened for a particular property or phenotype. For example, essential genes as described above are discovered using such screen. Another example of a screen is for unhampered growth, or growth less hampered than untransformed cells under various conditions, such as higher salinity or osmotic pressure, higher temperature, presence of toxic or harmful substances, e.g. herbicidal compounds. After such screen, the double-stranded RNA or the DNA molecule encoding the double-stranded RNA is recovered and the sequence of the complementary RNA fragments is determined, thus allowing to isolate the gene whose alteration of expression is responsible for the particular property or phenotype. Such gene is then used e.g. to improve crops by genetic transformation or to screen for novel chemicals.

Resistance or Tolerance to Viruses

In a preferred embodiment, the present invention results in cells, animals or plants which are virus resistant or tolerant. Viruses controlled using the present invention comprise but are not limited to dsDNA viruses, dsRNA viruses, plus-strand and minus-strand ssRNA viruses, ambisense RNA viruses and retroviruses. Preferably controlled are plant viruses, for example topsoviruses, potyviruses, potexviruses, tobamoviruses, luteoviruses, cucumoviruses, bromoviruses, closteorviruses, tombusviruses and furoviruses. Additional classes of viruses which are controllable using the present invention are described in Zacomer et al. (1995) Journal of General Virology, 76: 231–247 and in Martelli (1992) Plant Disease, 76: 436–441, both of which are incorporated herein in their entirety. Preferred DNA sequences of the present invention comprise the viral genome or any portion of the viral genome. Prefered are e.g. viral coat proteins or portions thereof, viral nucleocapsid proteins or portions thereof, viral replicases or portions thereof, movement proteins or portions thereof and the like. Additional DNA sequences are described in co-pending U.S. application Ser. No. 08/624,581 issued on May 25, 1999 as U.S. Pat. No. 5,907,084, incorporated herein by reference in its entirety. Other preferred DNA sequences include portions of the viral genome not translated into proteins, e.g. 5' or 3' untranslated regions.

Preferably, a method of the present invention leads to resistance or tolerance to a broad-spectrum of viruses. For example, a method of the present invention leads to resistance or tolerance to the virus encoded by the viral genome and other viruses in the same virus class, group or genus. Alternatively, a method of the present invention leads to resistance or tolerance to the virus encoded by the viral genome and other isolates of the same virus. Also, a method of the present invention leads to resistance or tolerance to the virus encoded by the viral genome and other viruses in the same virus group or genus in different species, preferably in related species, preferably species in which such viruses exist. Optionally, more than one pair of sense and antisense RNA fragments which are capable of forming a dsRNA are used. Such pairs are for example derived from the same viral genome, but from different portions of the same viral genome. Alternatively, such pairs are derived from different viral genomes. Thus, resistance or tolerance to different viruses classes, groups or genera is achieved using the present invention.

Plant cells and plants derived thereof, which are virus resistant or tolerant are preferably dicotyledonous plant. For example, methods to confer resistance or tolerance to furoviruses (see e.g. Rush and Heidel (1995) Plant Disease 79: 868–875, incorporated herein by referance in its entirety) for example in sugar beet and canola is disclosed in the present invention and described in further details for BNYVV, the causal agent of rhizomania (crazy roots) in sugar-beet, in Example 9. Also methods to confer resistance or tolerance to "virus yellow" (see e.g. CRC Handbook on Disease of Sugar Beet, Volume II, pp. 35–52) for example BMYV and beet western yellows virus (BWYV) that infect sugar beet and oilseed rape, respectively (see Example 8).

Methods of the present invention also confer tolerance or resistance to viruses in monocotyledonous plants. For example, using the teachings of the present invention and of U.S. Pat. No. 5,569,828 tolerance or resistance to Maize chlorotic dwarf virus is obtained. Similarly, using the teachings of the present invention of U.S. Pat. No. 5,428,144 tolerance or resistance to Maize dwarf mosaic virus is achieved.

Plant Transformation Technology

DNA molecules of the present invention are incorporated in plant or bacterial cells using conventional recombinant DNA technology. Generally, a DNA molecule of the present invention is comprised in a transformation vector. A large number of such vector systems known in the art are used, such as plasmids, bacteriophage viruses and other modified viruses. The components of the expression system are also modified, e.g. to increase expression of the sense and antisense RNA fragments. For example, truncated sequences, nucleotide substitutions or other modifications are employed. Expression systems known in the art are used to transform virtually any crop plant cell under suitable conditions. A transgene comprising a DNA molecule of the present invention is preferably stably transformed and integrated into the genome of the host cells. In another preferred embodiment, the transgene comprising a DNA molecule of the present invention is located on a self-replicating vector. Examples of self-replicating vectors are viruses, in particular gemini viruses. Transformed cells are preferably regenerated into whole plants.

Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, *Arabidopsis*, and woody plants such as coniferous and deciduous trees. Once a desired nucleotide sequence has been transformed into a particular plant species, it may be propagated in that species or moved into other varieties of the same species, particularly including commercial varieties, using traditional breeding techniques.

A. Requirements for Construction of Plant Expression Cassettes

Gene sequences intended for expression in transgenic plants are first assembled in expression cassettes behind a suitable promoter expressible in plants. The expression cassettes may also comprise any further sequences required or selected for the expression of the transgene. Such sequences include e.g., but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described infra. The following is a description of various components of typical expression cassettes.

1. Promoters

The selection of the promoter used in expression cassettes determine the spatial and temporal expression pattern of the transgene in the transgenic plant. Selected promoters express transgenes in specific cell types (such as leaf epidermal cells, mesophyll cells, root cortex cells) or in specific tissues or organs (roots, leaves or flowers, for example) and the selection reflects the desired location of accumulation of the gene product. Alternatively, the selected promoter drives expression of the gene under various inducing conditions. Promoters vary in their strength, i.e., ability to promote transcription. Depending upon the host cell system utilized, any one of a number of suitable promoters known in the art is used. For example, for constitutive expression, the CaMV 35S promoter, the rice actin promoter, or the ubiquitin promoter are used. For example, for regulatable expression, the chemically inducible PR-1 promoter from tobacco or *Arabidopsis* is used (see, e.g., U.S. Pat. No. 5,689,044).

A preferred category of promoters is that which is wound inducible. Numerous promoters have been described which are expressed at wound sites. Preferred promoters of this kind include those described by Stanford et al. Mol. Gen. Genet. 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993).

Preferred tissue specific expression patterns include green tissue specific, root specific, stem specific, and flower specific. Promoters suitable for expression in green tissue include many which regulate genes involved in photosynthesis, and many of these have been cloned from both monocotyledons and dicotyledons. A preferred promoter is the maize PEPC promoter from the phosphoenol carboxylase gene (Hudspeth & Grula, Plant Molec. Biol. 12: 579–589 (1989)). A preferred promoter for root specific expression is that described by de Framond (FEBS 290: 103–106 (1991); EP 0 452 269 and a further preferred root-specific promoter is that from the T-1 gene provided by this invention. A preferred stem specific promoter is that described in U.S. Pat. No. 5,625,136 and which drives expression of the maize trpA gene.

Preferred embodiments of the invention are transgenic plants expressing nucleotide sequence in a root-specific fashion. Further preferred embodiments are transgenic plants expressing the nucleotide sequence in a wound-inducible or pathogen infection-inducible manner.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These are used in both monocotyledonous and dicotyledonous plants.

3. Sequences for the Enhancement or Regulation of Expression

Numerous sequences have been found to enhance gene expression from within the transcriptional unit and these sequences can be used in conjunction with the genes of this invention to increase their expression in transgenic plants. For example, various intron sequences such as introns of the maize AdhI gene have been shown to enhance expression, particularly in monocotyledonous cells. In addition, a number of non-translated leader sequences derived from viruses are also known to enhance expression, and these are particularly effective in dicotyledonous cells.

4. Coding Sequence Optimization

The coding sequence of the selected gene may be genetically engineered by altering the coding sequence for optimal expression in the crop species of interest. Methods for modifying coding sequences to achieve optimal expression in a particular crop species are well known (see, e.g. Perlak et al., *Proc. Natl. Acad. Sci. USA* 88: 3324 (1991); and Koziel et al., *Bio/technol.* 11: 194 (1993)).

In another preferred embodiment, a DNA molecule of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45). The presence of cloning sites between these markers allowed creation of a plastid targeting vector for introduction of foreign DNA molecules (Staub, J. M., and Maliga, P. (1993) *EMBO J.* 12, 601–606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913–917). Previously, this marker had been used successfully for high-frequency transformation of the plastid genome of the green alga *Chlamydomonas reinhardtii* (Goldschmidt-Clermont, M. (1991) *Nucl. Acids Res.* 19: 4083–4089). Other selectable markers useful for plastid transformation are known in the art and encompassed within the scope of the invention.

Plastid expression, in which genes are inserted by homologous recombination into the several thousand copies of the circular plastid genome present in each plant cell. In a preferred embodiment, a DNA of the present invention is inserted into a plastid targeting vector and transformed into the plastid genome of a desired plant host. Plants homoplasmic for plastid genomes containing the DNA molecule of the present invention are obtained, and are preferentially capable of high expression of the DNA molecule. Preferably, sense and antisense RNA fragments encoded by the DNA molecule are capable of pairing and of forming a double-stranded RNA molecules in plant plastids to to alter the expression of plastid genes. In a preferred embodiment, the sense and antisense fragments do not comprise any mismatch in the complementary region. In another preferred embodiment, the sense and antisense fragments comprise at least one mismatch in the complementary region. In this case, the DNA sequences in the DNA molecule encoding the RNA fragments are not capable of recombining with each other.

B. Construction of Plant Transformation Vectors

Numerous transformation vectors available for plant transformation are known to those of ordinary skill in the plant transformation arts, and the genes pertinent to this invention can be used in conjunction with any such vectors. The selection of vector depends upon the preferred transformation technique and the target species for transformation. For certain target species, different antibiotic or herbicide selection markers are preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Typical vectors suitable for *Agrobacterium* transformation include the binary vectors pCIB200 and pCIB2001, as well as the binary vector pCIB10 and hygromycin selection derivatives thereof. (See, for example, U.S. Pat. No. 5,639,949).

2. Vectors Suitable for Non-*Agrobacterium* Transformation

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Typical vectors suitable for non-*Agrobacterium* transformation include pCIB3064, pSOG19, and pSOG35. (See, for example, U.S. Pat. No. 5,639,949).

C. Transformation Techniques

Once the DNA sequence of interest is cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, micro-injection, and microprojectiles. In addition, bacteria from the genus *Agrobacterium* can be utilized to transform plant cells.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This is accomplished by PEG or electroporation mediated uptake, particle bombardment-mediated delivery, or microinjection. In each case the transformed cells are regenerated to whole plants using standard techniques known in the art.

Transformation of most monocotyledon species has now also become routine. Preferred techniques include direct gene transfer into protoplasts using PEG or electroporation techniques, particle bombardment into callus tissue, as well as *Agrobacterium*-mediated transformation.

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by Sambrook, et al., *Molecular Cloning*, eds., Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Example 1

Regulation of the Expression of a Luciferase Gene

A. Construction of a Chimeric DNA Molecule Encoding a Luciferase RNA Duplex

A 738 bp "sense" oriented fragment of the firefly luciferase gene from plasmid pLuc+ (Promega) is amplified from pPH108 plasmid DNA using oligonucleotide primers ds_Luc1 (5'-CGC GGA TCC TGG AAG ACG CCA AAA ACA-3', SEQ ID NO:1; BamHI restriction site underlined) and ds_Luc2 (5'-CGG AAG CTT AGG CTC GCC TAA TCG CAG TAT CCG GAA TG-3', SEQ ID NO:2; HindIII restriction site underlined). TurboPfu thermostable DNA polymerase (Stratagene) is used in 50 ul reactions according to the manufacturers protocol with five cycles of 95° C./1 min, 55° C./1.5 min, 72° C./2 min followed by twenty five cycles of 95° C./1 min, 72° C./3.5 min. In a similar manner a 737 bp "antisense" oriented fragment of the firefly luciferase gene from plasmid pLuc+ is amplified by PCR from pPH108 plasmid DNA using oligonucleotide primers ds_Luc3 (5'-CGG TCT AGA GGA AGA CGC CAA AAA CAT A-3', SEQ ID NO:3; XbaI restriction site underlined) and ds_Luc2 (5'-CGG AAG CTT AGG CTC GCC TAA TCG CAG TAT CCG GAA TG-3', SEQ ID NO:4; HindIII restriction site underlined). The resulting DNA fragments are purified by electrophoresis through a 1% Tris-acetate gel made from low-melting point agarose (FMC) followed by phenol-chloroform extraction of the excised gel slices containing the PCR products. DNA from the sense product (ds_Luc1/2) is digested with BamHI and HindIII and DNA from the antisense product (ds_Luc3/2) is digested with XbaI and HindIII according to standard methods (restriction enzymes were obtained from New England Biolabs). The resulting sticky-ended DNA fragments are gel purified as described above. A DNA fragment containing the mas 1' promoter (Velten et al. (19984) EMBO J. 3: 2723–2730) is obtained by digesting plasmid CSA104 with EcoRI and HincII and purifying a 564 bp DNA fragment. This fragment is redigested with BamHI and the 484 bp EcoRI-BamHI sub-fragment containing the mas 1' promoter isolated and gel purified. In order to construct plasmid pPH169, DNA from cloning vector pLitmus29 (New England Biolabs) is digested with EcoRI and XbaI, and the isolated fragment is ligated in a four-way reaction using T4 DNA ligase (New England Biolabs) to the mas 1' promoter EcoRI-BamHI fragment and the sense (BamHI-HindIII) and antisense (HindIII-XbaI) ds_Luc luciferase gene fragments.

In order to construct binary vector pPH170 for *Agrobacterium*-mediated plant transformation with the ds_Luc1/2/3 RNA duplex construct, DNA from binary plasmid pSGCHC1 carrying a kanamycin resistance gene for bacterial selection and a hygromycin resistance gene for transgenic plant selection is digested with EcoRI and XbaI. The resulting 11.6 kb isolated fragment from pSGCHC1 is ligated in a four-way reaction using T4 DNA ligase (New England Biolabs) to the mas 1' promoter EcoRI BamHI fragment and the sense (BamHI-HindIII) and antisense (HindIII-XbaI) ds_Luc luciferase gene fragments.

Transformation of *Agrobacterium* and Vacuum-Infiltration of *Arabidopsis* Plants Plasmids pPH170 is introduced into *Agrobacterium tumafaciens* GV3101 by electroporation and transformed colonies selected and amplified. Four to five week old plants of *Arabidopsis thaliana* mutant lines expressing luciferase either consitutively (UBQ3 promoter (Norris et al. (1993) PMB 21: 895–906)/UBQ3+CaMV 35S 5' UTR/luc+; pPH108) or inducibly (*Arabidopsis* PR-1 promoter/luc+; pPH135, line 6E) are vacuum infiltrated with *Agrobacterium* clones carrying the pPH170 binary T-DNA vector. Transformed plants are co-selected on hygromycin and kanamycin and grown under controlled phytotron conditions for determination of luciferase activity. In addition, luciferase activity in the pPH135-6E background is assessed 48 hr after induction with BTH (BTH treatment essentially as described in Lawton et al. Plant J. 10: 71–82). Luciferase activity is quantified using a luminescence-based assay in tissue extracts following the addition of luciferin substrate. Luciferase activity is also monitored in planta using a CCD-cooled video imaging system (Hamamatsu).

Example 2

Regulation of the Expression of the *Arabidopsis* GL1 Gene

The GL1 gene encodes a myb-like transcription factor that is required for initiation of normal trichome (leaf hair) formation (Oppenheimer et al. (1991) Cell 67: 483–493). Knock out of GL1 expression early in development results in plants lacking trichomes. The knockout phenotype is easy to identify in young seedlings and is not lethal. Three vectors for constitutive expression and three vectors for Gal4CI-regulated expression are constructed. The three different vectors to test for each promoter are sense (+) expression, antisense (−) expression, and duplex (+/−) RNA expression of a GL1 gene fragment. The (+) and (−) vectors are controls to compare for their effect on expression of GL1. In each case a 5' fragment from bases #739 to #1781 of the GL1 sequence (GenBank Accession M79448) are used for vector construction.

A. Gal14CI-Regulated Expression

The GL1 gene fragments is cloned into the crossing-inducible vector construct pJG304-1 as NcoI-SacI fragments. Plasmid pJG304 is derived from pBSSK+. Plasmid pBS SK+ (Stratagene, LaJolla, Calif.) is linearized with SacI, treated with mung bean nuclease to remove the SacI site, and re-ligated with T4 ligase to make pJG201. The 10XGAL4 consensus binding site/CaMV $^{35}$S minimal promoter/GUS gene/CaMV terminator cassette is removed from pAT71 with KpnI and cloned into the KpnI site of pJG201 to make pJG304. Plasmid pJG304 is partially digested with restriction endonuclease Asp718 to isolate a full-length linear fragment. This fragment is ligated with a molar excess of the 22 base oligonucleotide JG-L (5'-GTA CCT CGA G TC TAG ACT CGA G-3', SEQ ID NO:5). Restriction analysis is used to identify a clone with this linker inserted 5' to the GAL4 DNA binding site, and this plasmid is designated pJG304ΔXhoI.

The NcoI and SacI sites are added to the ends of (+) and (−) fragments by synthesizing PCR primers with the appropriate restriction sites to the 5' termini. The (+/) GL1 fragment is produced by first producing two fragment: a (+) fragment with the NcoI site at the 5' terminus and a HindIII site at the 3' terminus and a (−) fragment with a HindIII site at the 5' terminus and a SacI site at the 3' terminus. The duplex unit is produced by ligation of the resulting fragments at the EcoRI site. The expression unit contains the Gal4 DNA binding domain, followed by a minimal TATA sequence, and the GL1 gene fragment oriented either (+), (−) or (+/−).

B. Constitutive Expression

The mas 1' promoter of mannopine synthase from *Agrobacterium*(ref), a relatively strong and constitutive in dicot plants is used. As above, the GL (+), (−), and (+/−) fragments are ligated behind the 1' promoter in pBluescript. The three different expression cassettes are ligated into pCIB200 as EcoRI/SalI fragments (Uknes et al. (1993) Plant Cell 5: 159–169).

Example 3

Regulation of the Expression of the Cystathionine Beta Lyase Gene

The Cystathionine Beta Lyase (CBL) Gene encodes a step in the methionine biosynthesis pathway. The effect of the regulation of its expression in plants is tested using sense and antisense constructs, and double-stranded RNA constructs.

A. Antisense construct: binary BASTA vector pJG261 is used containing a fragment from the pJG304ΔXhoI vector with an insertion of part of the CBL gene in an antisense orientation (nucleotides #13-1159, Genbank accession #L40511).

B. Sense construct: same as antisense construct, except the CBL fragment is in the opposite orientation. This construct contains the ATG start codon and most of the CBL ORF and serves as a control for regulation of the expression of the CBL gene.

C. Double-stranded RNA construct: A CBL gene fragment (#13-1159) in the sense orientation is inserted into the SalI site of vector pJG304-1 downstream of the antisense orientation version of the CBL gene. A linker of about 10 bp is present between the two copies of CBL.

Example 4

Requirements for Construction of Plant Expression Cassettes

Gene sequences intended for expression in transgenic plants are firstly assembled in expression cassettes behind a suitable promoter and upstream of a suitable transcription terminator. All requirement for constructions of plant expression cassettes apply to the DNA molecules of the present invention and are carried out using techniques well-known in the art.

Promoter Selection

The selection of promoter used in expression cassettes determines the spatial and temporal expression pattern of the DNA molecule in the transgenic plant. Selected promoters express DNA molecule in specific cell types (such as leaf epidermal cells, meosphyll cells, root cortex cells) or in specific tissues or organs (roots, leaves or flowers, for example) and this selection reflects the desired location of biosynthesis of a RNA fragment encoded by the DNA molecule. Alternatively, the selected promoter may drive expression of the DNA molecule under a light-induced or other temporally regulated promoter. A further alternative is that the selected promoter be chemically regulated. This provides the possibility of inducing the expression of the DNA molecule only when desired and caused by treatment with a chemical inducer.

Transcriptional Terminators

A variety of transcriptional terminators are available for use in expression cassettes. These are responsible for the termination of transcription and, preferably, correct polyadenylation. Appropriate transcriptional terminators and those which are known to function in plants and include the CaMV 35S terminator, the tml terminator, the nopaline synthase terminator, the pea rbcS E9 terminator. These can be used in both monocoylyedons and dicotyledons.

Sequences for the Enhancement or Regulation of Expression

Numerous sequences have been found to enhance gene expression from within the transcriptional unit and these sequences can be used in conjunction with the DNA molecule of this invention to increase its expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 is found to be particularly effective and enhanced expression in fusion constructs with the chloramphenicol acetyltransferase gene (Callis et al., Genes Develep 1: 1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15; 65–79 (1990)).

Example 5

Examples of Expression Cassette Construction

The present invention encompasses the expression of a DNA molecule of the present invention under the regulation of any promoter which is expressible in plants, regardless of the origin of the promoter. Therefore the DNA molecule is inserted into any of the expression cassette using techniques well-known in the art. These expression cassettes can then be easily transferred to the plant transformation vectors described below.

Furthermore, the invention also encompasses the use of any plant-expressible promoter in conjunction with any further sequences required or selected for the expression of the DNA molecule. Such sequences include, but are not restricted to, transcriptional terminators, extraneous sequences to enhance expression (such as introns [e.g. Adh intron 1], viral sequences [e.g. TMV-Ω]).

Constitutive Expression: the CaMV 35S Promoter

Construction of the plasmid pCGN1761 is described in the published patent application EP 0 392 225. pCGN1761 contains the "double" 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or gene sequences (including microbial ORF sequences) within its polylinker for the purposes of their expression under the control of the 35S promoter in transgenic plants. The entire 35S promoter-gene sequence-tml terminator cassette of such a construction can be excised by HindIII, SphI, SalI, and XbaI sites 5' to the promoter and XbaI, BamHI and BglI sites 3' to the terminator for transfer to transformation vectors. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter.

Accordingly, a DNA molecule of the present invention is inserted into pCGN1761ENX for constitutive expression under the control of the CaMV 35S promoter.

Expression Under a Chemically Regulatable Promoter

This section describes the replacement of the double 35S promoter in pCGN1761ENX with any promoter of choice; by way of example the chemically regulated PR-1a promoter is described. The promoter of choice is preferably excised from its source by restriction enzymes, but can alternatively be PCR-amplified using primers which carry appropriate terminal restriction sites. Should PCR-amplification be undertaken, then the promoter should be resequenced to check for amplification errors after the cloning of the amplified promoter in the target vector. The chemically regulatable tobacco PR-1a promoter is cleaved from plasmid pCIB1004 (see EP 0 332 104) and transferred to plasmid pCGN1761ENX. pCIB1004 is cleaved with NcoI and the resultant 3' overhang of the linearized fragment is rendered blunt by treatment with T4 DNA polymerase. The fragment is then cleaved with HindIII and the resultant PR-1a promoter containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites.

A DNA molecule of the present invention is inserted into this vector, and the fusion product (i.e. promoter-gene-terminator) is subsequently transferred to any selected transformation vector, including those described in this application, thus providing for chemically inducible expression of the DNA molecule.

Constitutive Expression: the Actin Promoter

Several isoforms of actin are known to be expressed in most cell types and consequently the actin promoter is a good choice for a constitutive promoter. In particular, the promoter from the rice Act1 gene has been cloned and characterized (McElroy et al. Plant Cell 2: 163–171 (1990)). A 1.3 kb fragment of the promoter is found to contain all the regulatory elements required for expression in rice protoplasts. Furthermore, numerous expression vectors based on the Act1 promoter have been constructed specifically for use in monocotyledons (McElroy et al. Mol. Gen. Genet. 231: 150–160 (1991)). These incorporate the Act1-intron 1, Adh1 5' flanking sequence and Adh1-intron 1 (from the maize alcohol dehydrogenase gene) and sequence from the CaMV 35S promoter. Vectors showing highest expression are fusions of 35S and the Act1 intron or the Act1 5' flanking sequence and the Act1 intron. The promoter expression cassettes described by McElroy et al. (Mol. Gen. Genet. 231: 150–160 (1991)) is easily modified for the expression of a DNA molecule of the present invention and are particularly suitable for use in monocotyledonous hosts. For example, promoter containing fragments are removed from the McElroy constructions and used to replace the double 35S promoter in pCGN1761ENX, which is then available for the insertion or specific gene sequences. The fusion genes thus constructed are transferred to appropriate transformation vectors. In a separate report the rice Act1 promoter with its first intron has also been found to direct high expression in cultured barley cells (Chibbar et al. Plant Cell Rep. 12: 506–509 (1993)).

A DNA molecule of the present invention is inserted downstream of such promoter, and the fusion products (i.e. promoter-gene-terminator) are subsequently transferred to any selected transformation vector, including those described in this application.

Constitutive Expression: the Ubiquitin Promoter

Ubiquitin is another gene product known to accumulate in many cell types and its promoter has been cloned from several species for use in transgenic plants (e.g. sunflower—Binet et al. Plant Science 79: 87–94 (1991), maize—Christensen et al. Plant Molec. Biol. 12: 619–632 (1989)). The maize ubiquitin promoter has been developed in transgenic monocot systems and its sequence and vectors constructed for monocot transformation are disclosed in the patent publication EP 0 342 926. Further, Taylor et al. (Plant Cell Rep. 12: 491–495 (1993)) describe a vector (pAHC25) which comprises the maize ubiquitin promoter and first intron and its high activity in cell suspensions of numerous monocotyledons when introduced via microprojectile bombardment. The ubiquitin promoter is clearly suitable for the expression of a DNA molecule of the present invention in transgenic plants, especially monocotyledons. Suitable vectors are derivatives of pAHC25 or any of the transformation vectors described in this application, modified by the introduction of the appropriate ubiquitin promoter and/or intron sequences.

A DNA molecule of the present invention is therefore inserted into any of these vector, and the fusion products (i.e. promoter-gene-terminator) are used for transformation of plants, resulting in constitutive expression of the DNA molecule.

Root Specific Expression

A preferred pattern of expression for a DNA molecule of the instant invention is root expression. Expression of the nucleotide sequence only in root tissue has the advantage of altering the expression of a target gene only in roots, without a concomitant alteration of its expression in leaf and flower tissue and seeds. A suitable root promoter is that described by de Framond (FEBS 290: 103–106 (1991)) and also in the published patent application EP 0 452 269. This promoter is transferred to a suitable vector such as pCGN1761ENX and the DNA molecule is inserted into such vector. The entire promoter-gene-terminator cassette is subsequently transferred to a transformation vector of interest.

Wound Inducible Promoters

Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. (supra) describe the 5' upstream sequences of the dicotyledonous potato wun1 gene. Xu et al. (supra) show that a wound inducible promoter from the dicotyledon potato (pin2) is active in the monocotyledon rice. Further, Rohrmeier & Lehle (supra) describe the cloning of the maize Wip1 cDNA which is wound induced and which can be used to isolated the cognate promoter using standard techniques. Similarly, Firek et al. (supra) and Warner et al. (supra) have described a wound induced gene from the monocotyledon *Asparagus officinalis* which is expressed at local wound and pathogen invasion sites. Using cloning techniques well known in the art, these promoters can be transferred to suitable vectors, fused to a DNA molecule of this invention, and used to express these genes at the sites of insect pest infection.

Pith Preferred Expression

Patent application WO 93/07278 describes the isolation of the maize trpA gene which is preferentially expressed in pith cells. Using standard molecular biological techniques, this promoter or parts thereof, can be transferred to a vector such as pCGN1761 where it can replace the 35S promoter and be used to drive the expression of a DNA molecule of the present invention in a pith-preferred manner. In fact, fragments containing the pith-preferred promoter or parts thereof are transferred to any vector and modified for utility in transgenic plants. Pith preferred expression of the DNA molecule is achieved by inserting the DNA molecule in such vector.

Pollen-Specific Expression

Patent Application WO 93/07278 further describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, is transferred to a vector such as pCGN1761 where it replaces the 35S promoter and is used to drive the expression of a DNA molecule of the present invention in a pollen-specific manner. In fact fragments containing the pollen-specific promoter or parts thereof can be transferred to any vector and modified for utility in transgenic plants.

Leaf-Specific Expression

A maize gene encoding phosphoenol carboxylase (PEPC) has been described by Hudspeth & Grula (Plant Molec Biol 12: 579–589 (1989)). Using standard molecular biological techniques the promoter for this gene is used to drive the expression of a DNA molecule of the present invention in a leaf-specific manner in transgenic plants.

Example 6

Construction of Plant Transformation Vectors

Numerous transformation vectors are available for plant transformation, and a DNA molecule of this invention is inserted into any of the expression cassettes described above, such that they are capable of expressing the DNA molecule in desirable cells, under appropriate conditions. A nucleotide sequence-containing expression cassette is then incorporated into any appropriate transformation vector described below.

The selection of vector for use will depend upon the preferred transformation technique and the target species for transformation. For certain target species, different antibiotic or herbicide selection markers may be preferred. Selection markers used routinely in transformation include the nptII gene which confers resistance to kanamycin and related antibiotics (Messing & Vierra, Gene 19: 259–268 (1982); Bevan et al., Nature 304:184–187 (1983)), the bar gene which confers resistance to the herbicide phosphinothricin (White et al., Nucl Acids Res 18: 1062 (1990), Spencer et al. Theor Appl Genet 79: 625–631(1990)), the hph gene which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)).

(1) Construction of Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below the construction of two typical vectors is described.

Construction of pCIB200 and pCIB2001

The binary vectors pCIB200 and pCIB2001 are used for the construction of recombinant vectors for use with *Agrobacterium* and is constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982); Bevan et al., Nature 304: 184–187 (1983); McBride et al., Plant Molecular Biology 14: 266–276 (1990)). XhoI linkers are ligated to the EcoRV fragment of pCIB7 which contains the left and right T-DNA borders, a plant selectable nos/nptII chimeric gene and the pUC polylinker (Rothstein et al., Gene 53: 153–161 (1987)), and the XhoI-digested fragment is cloned into SalI-digested pTJS75kan to create pCIB200 (see also EP 0 332 104). pCIB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Any one of the plant expression cassettes described above and comprising a DNA molecule of the present invention are inserted into pCIB2001, preferably using the polylinker.

Construction of pCIB10 and Hygromycin Selection Derivatives thereof

The binary vector pCIB10 contains a gene encoding kanamycin resistance for selection in plants, T-DNA right and left border sequences and incorporates sequences from the wide host-range plasmid pRK252 allowing it to replicate in both *E. coli* and *Agrobacterium*. Its construction is described by Rothstein et al. (Gene 53: 153–161 (1987)). Various derivatives of pCIB10 have been constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717). This vectors is used transform an expression cassette comprising a DNA molecule of the present invention.

(2) Construction of Vectors Suitable for Non-*Agrobacterium* Transformation.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques which do not rely on *Agrobacterium* include transformation via particle bombardment, protoplast uptake (e.g. PEG and electroporation), microinjection or pollen transformation (U.S. Pat. No. 5,629,183). The choice of vector depends largely on the preferred selection for the species being transformed. Below, the construction of some typical vectors is described.

Construction of pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al. EMBO J. 6: 2519–2523 (1987)). This generated pCIB3064 which comprises the bar gene under the control of the CaMV 35S promoter and terminator for herbicide selection, a gene fro ampicillin resistance (for selection in *E. coli*) and a polylinker with the unique sites SphI, PstI, HindIII, and BamHI. This vector is suitable for the cloning of plant expression cassettes containing their own regulatory signals to direct expression of a DNA molecule of the present invention.

Construction of pSOG19 and pSOG35 pSOG35 is a transformation vector which utilizes the *E. coli* gene dihydrofolate reductase (DHFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250 bp fragment encoding the *E. coli* dihydrofolate reductase type II gene is also amplified by PCR and these two PCR fragments are assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences, in particular a DNA molecule of the present invention.

Example 7

Chloroplast Transformation

Transformation Vectors

For expression of a DNA molecule of the present invention in plant plastids, plastid transformation vector pPH143 (WO 97/32011, example 36) is used. The DNA molecule is inserted into pPH143 thereby replacing the PROTOX coding sequence. This vector is then used for plastid transformation and selection of transformants for spectinomycin resistance. Alternatively, the DNA molecule is inserted in pPH143 so that it replaces the aadH gene. In this case, transformants are selected for resistance to PROTOX inhibitors.

Chloroplast Transformation

Seeds of *Nicotiana tabacum* c.v. 'Xanthi nc' were germinated seven per plate in a 1" circular array on T agar medium and bombarded 12–14 days after sowing with 1 µm tungsten particles (M10, Biorad, Hercules, Calif.) coated with DNA from plasmids pPH143 and pPH145 essentially as described (Svab, Z. and Maliga, P. (1993) *PNAS* 90, 913–917). Bombarded seedlings were incubated on T medium for two days after which leaves were excised and placed abaxial side up in bright light (350–500 µmol photons/m$^2$/s) on plates of RMOP medium (Svab, Z., Hajdukiewicz, P. and Maliga, P. (1990) *PNAS* 87, 8526–8530) containing 500 µg/ml spectinomycin dihydrochloride (Sigma, St. Louis, Mo.). Resistant shoots appearing underneath the bleached leaves three to eight weeks after bombardment were subcloned onto the same selective medium, allowed to form callus, and secondary shoots isolated and subcloned. Complete segregation of transformed plastid genome copies (homoplasmicity) in independent subclones was assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) was separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

Example 8

Construction of a Chimeric Gene Cassette Encoding Sense and Antisense RNA Fragment for the Coat Protein Gene from BWYV, Driven by the RoIC Promoter An 0.6 Kb 'sense' oriented fragment of the beet western yellows virus (BWYV), a so-called virus yellow, coat protein (CP) gene is amplified from plasmid pZU046 using primers HiNK025bis (5'-CAA TTA CCATGG ACA CGG TCG TGG-3', SEQ ID NO:6; NcoI restriction site underlined), and HiNK226 (5'-GCC AAA TGT TTG AAC GCTGCAGCC TAT TTG-3', SEQ ID NO:7; PstI restriction site underlined). Taq DNA Polymerase (Life Technologies) is used in 25 µl reactions according to the manufacturer's prescription applying 30 cycles of 94° C./30 sec, 55° C./30 sec, 72° C./90 sec (+2 sec/cycle). The resulting PCR fragment is purified by electrophoresis through a 1% Tris-acetate gel made from Seakem GTG agarose (FMC), followed by an extraction of the gel slices containing the PCR product with QIAquick Gel Extraction Kit (QIAGEN). The PCR product is subsequently digested with NcoI and PstI (all restriction enzymes were supplied by Life Technologies) according to standard methods and again gel purified. Plasmid pHiNK097 is digested with NcoI and PstI to remove the insert and to recover the 4.3 Kb vector that carries the RoIC promoter and the Nos terminator, and ligated to the NcoI-PstI digested PCR product using T4 DNA ligase (Life Technologies). The resulting clone is named pHiNK138.

In a similar manner as described above a 1.4 Kb 'antisense' oriented BWYV CP fragment is amplified from plasmid pZU174A using primers HiNK251 (5'-CTC CCA GGT TGA GAC TGC CCTGCAGTG CCC A-3', SEQ ID NO:8; PstI restriction site underlined) and HiNK228 (5'-TTA CCATGCATA CGG TCG TGG GTA GG-3', SEQ ID NO:9; NsiI restriction site underlined). Upon gel purification the PCR product is digested with NsiI and PstI. The 4.9 Kb plasmid pHiNK138 is linearised with PstI, the digested vector and PCR fragment are gel purified, followed by the bidirectional ligation of the PCR fragment into pHiNK138. The orientation generating the duplex RNA for the CP gene was identified by restriction site analysis, yielding plasmid pHiNK152 in which the inverted repeat consists of the 0.6 Kb CP gene separated by the 0.7 Kb spacer sequence derived from the BWYV genome downstream of the CP gene, referred to as ORF6. The spacer sequence is in the antisense orientation.

Example 9

Construction of a Chimeric Gene Cassette Encoding a Sense and Antisense RNA FRAGMENT for the Replicase Gene from BNYVV, Driven by the *Arabidopsis* Ubi3int Promoter Total RNA was extracted from sugar beet root infected by the beet necrotic yellow vein virus (BNYVV), a furovirus, using the RNAeasy Plant mini kit from QIAGEN. In order to amplify the 3' end of the BNYVV replicase gene (RNA1) the RNA was reverse transcribed to produce a cDNA using the Superscript™II RNAse H⁻ Reverse Transcriptase (RT) (Life Technologies) and the reverse primer HiNK285 (5'-TCG TAG AAG AGAATTCAC CCA AAC TAT CC-3', SEQ ID NO:10). Primer HiNK285 is located between nucleotides 6378 and 6405 of the BNYVV RNA1 sequence (accession number D00115) and designed to introduce an EcoRI site. The RT reaction is subsequently used as template for two PCR reactions:

Reaction A using primer HiNK283 (5'-AAG AAT TGC AGG ATC CAC AGG CTC GGT AC-3', SEQ ID NO:11) located between nucleotides 5168 bp and 5178 bp of BNYVV RNA1 designed to introduce a BamHI site, and primer HiNK284 (5'-TTC CAA C GAATTCGG TCT CAG AC A-3', SEQ ID NO:12) located between nucleotides 5597 and 5620 of BNYVV RNA1 designed to introduce an EcoRI site.

Reaction B using primer HiNK283 in combination with primer HiNK285, both described above.

The thus obtained RT-PCR products share the BNYVV RNA1 sequence between nucleotides 5168–5620 that constitutes the future RNA duplex. The future spacer sequence corresponds to nucleotides 5621–6405 bp of BNYVV RNA1 present at the RT-PCR product obtained with primers HiNK283 and HiNK285.

Taq DNA Polymerase (Life Technologies) is used in 25 µl reactions according to the suppliers's prescription applying 30 cycles of 94° C./30 sec, 55° C./30 sec, 72° C./90 sec(+2 sec/cycle). The resulting RT-PCR products are purified by electrophoresis through a 1% Tris-acetate gel made from Seakem GTG agarose (FMC), followed by an extraction of the gel slices containing the amplification products with the QIAquick Gel Extraction Kit (QIAGEN). After gel purification, the RT-PCR products are digested with restriction enzymes BamHI and EcoRI (Life Technologies) according to standard methods and purified as described above.

Plasmid pHiNK173 is digested with BamHI to remove the insert and to recover the 4.7 Kb vector that carries the *Arabidopsis* Ubiquitin3 (Ubi3int) promoter and the Nos terminator. After digestion the vector DNA was precipitated and resuspended in water, dephosphorylated using the Thermosensitive Alkaline Phosphatase (Life Technologies) and purified by electrophoresis as described above. Finally the vector is added to a mixture of both RT-PCR products in a three-way ligation reaction using T4 DNA ligase (Life Technologies). The two resulting clones are named pHiNK181 (spacer in antisense orientation) and pHiNK184 (spacer in sense orientation).

In order to construct the binary vectors for the *Agrobacterium*-mediated transformation of sugar beet, DNA from binary vector pVictorHiNK carrying the phophomannose isomerase gene as selectable marker, as well as plasmids pHiNK181 and pHiNK184, are digested with with AscI and PacI (New England Biolabs) and the vector and insert fragments purified by electrophoresis as described above. The resulting 7.7 kb pVictorHiNK vector fragment is ligated using T4 DNA ligase (Life Technologies) to the gene cassettes encoding the duplex RNA for the BNYVV replicase gene yielding pHiNK187 (antisense spacer) and pHiNK188 (sense spacer) respectively.

The above disclosed embodiments are illustrative. This disclosure of the invention will place one skilled in the art in possession of many variations of the invention. All such obvious and foreseeable variations are intended to be encompassed by the appended claims.

What is claimed is:

1. A method for conferring resistance or tolerance to more than one virus selected from the group consisting of a furovirus, potyvirus, tospovirus, and cucomovirus upon a plant cell comprising the step of: introducing into a plant cell more than one pair of DNA sequences wherein for each pair, the first DNA sequence encodes a portion of the viral genome of a furovirus, potyvirus, tospovirus, or cucomovirus, and the second DNA sequence of the pair encodes a sequence that is antisense to the first DNA sequence, such that the RNA sequences encoded by the first and second DNA sequences of a pair form a double-stranded RNA molecule when expressed in said plant cell, resulting upon viral infection, in reduced expression of the portion of the viral genome from which the DNA sequences of that pair were derived, and wherein at least two of the introduced pairs of DNA sequences were derived from different viruses of said group, resulting in resistance or tolerance of said plant cell to more than one virus of said group.

2. The method of claim 1, wherein the first DNA sequence of a pair comprises a nucleotide sequence obtained from a viral coat protein gene, a viral nucleocapsid protein gene, a viral replicase gene, a movement protein gene or portions thereof.

3. The method of claim 1, wherein said first DNA sequence and said second DNA sequence of each pair are stably integrated in the genome of said cell.

4. The method of claim 1, wherein said first DNA sequence and said second DNA sequence of each pair are comprised in two different DNA molecules.

5. The method of claim 4, wherein said DNA sequences further comprise a first promoter operably linked to said first DNA sequence and a second promoter operably linked to said second DNA sequence of each pair.

6. The method of claim 1, wherein said first DNA sequence and said second DNA sequence of a pair are comprised in one DNA molecule.

7. The method of claim 6, wherein said first DNA sequence and said second DNA sequence of a pair are comprised in the same DNA strand of said DNA molecule.

8. The method of claim 7, wherein said RNA sequences encoded by said first and second DNA sequences of a pair are comprised in one RNA molecule.

9. The method of claim 8, wherein said RNA molecule is capable of folding such that said RNA sequences comprised therein form a double-stranded region.

10. The method of claim 8, wherein said DNA molecule further comprises a promoter operably linked to said first and said second DNA sequence.

11. The method of claim 10, wherein said promoter is a heterologous promoter.

12. The method of claim 10, wherein said promoter is a tissue-specific promoter.

13. The method of claim 10, wherein said promoter is a developmentally regulated promoter.

14. The method of claim 10, wherein said promoter is a constitutive promoter.

15. The method of claim 10, wherein said promoter is an inducible promoter.

16. The method of claim 8, wherein said DNA molecule further comprises a linker between the first and second DNA sequences.

17. The method of claim 16, wherein the linker comprises intron processing signals.

18. The method of claim 7, wherein said RNA sequences encoded by the first and second DNA sequences are comprised in two RNA molecules.

19. The method of claim 18, wherein said first DNA sequence is operably linked to a first promoter and said second DNA sequence is operably linked to a second promoter.

20. The method of claim 18, wherein said first DNA sequence and said second DNA sequence are operably linked to a bidirectional promoter.

21. The method of claim 7, wherein said first DNA sequence and said second DNA sequence are comprised in complementary strands of said DNA molecule.

22. The method of claim 21, wherein said first DNA sequence is the complementary DNA strand of said second DNA sequence in said DNA molecule.

23. The method of claim 22, wherein said DNA molecule further comprises a first promoter operably linked to said first DNA sequence.

24. A plant cell obtained by the method of claim 1, wherein said cell is resistant or tolerant to more than one virus selected from the group consisting of said furovirus, potyvirus, topsovirus and cucomovirus.

25. A plant comprising the plant cell of claim 24, wherein the plant is virus resistant or tolerant to more than one virus selected from the group consisting of said furovirus, potyvirus, tospovirus and cucomovirus.

26. A plant regenerated from the plant cell of claim 24, wherein the plant is resistant or tolerant to more than one virus selected from the group consisting of said furovirus, potyvirus, tospovirus and cucomovirus.

27. Seeds produced from the plant of claim 26, wherein said seeds are resistant or tolerant to more than one virus selected from the group consisting of said furovirus, potyvirus, tospovirus and cucomovirus and comprise said more than one pair of DNA sequences.

28. The method of claim 1, wherein one of said pairs of DNA sequences comprises a nucleotide sequence obtained from a furovirus replicase gene or portion thereof.

29. The method of claim 1, wherein one of said pairs of DNA sequences comprises a nucleotide sequence obtained from the beet necrotic yellow vein virus (BNYVV).

30. The method of claim 29, wherein said pair DNA sequences comprises a nucleotide sequence obtained from the replicase gene (RNA1) of the beet necrotic yellow vein virus or portion thereof.

31. The method of claim 30, wherein the portion of the replicase gene from BNYVV comprises the 3' end.

32. The method of claim 1, wherein one of said pairs of DNA sequences comprises a nucleotide sequence obtained from a potyvirus.

33. The method of claim 1, wherein one of said pairs of DNA sequences comprises a nucleotide sequence obtained from a tospovirus.

34. The method of claim 1, wherein one of said pairs of DNA sequences comprises a nucleotide sequence obtained from a cucomovirus.

35. Progeny obtained from the plant of claim 26, wherein said progeny are resistant or tolerant to more than one virus selected from the group consisting of said furovirus, potyvirus, tospovirus and cucomovirus, and wherein said progeny comprise said more than one pair of DNA sequences.

* * * * *

SEQUENCE LISTING

<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:
    oligonucleotide

<400> SEQUENCE: 1
cgcggatcct ggaagacgcc aaaaaca                               27

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence:
    oligonucleotide

<400> SEQUENCE: 2
cggaagctta ggctcgccta atcgcagtat ccggaatg                   38

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
cggtctagag gaagacgcca aaaacata                                        28

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
cggaagctta ggctcgccta atcgcagtat ccggaatg                             38

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
gtacctcgag tctagactcg ag                                              22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
caattaccat ggacacggtc gtgg                                            24

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gccaaatgtt tgaacgctgc agcctatttg                                      30

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
ctcccaggtt gagactgccc tgcagtgccc a                                    31

```
<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ttaccatgca tacggtcgtg ggtagg                                              26

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
tcgtagaaga gaattcaccc aaactatcc                                           29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
aagaattgca ggatccacag gctcggtac                                           29

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
ttccaacgaa ttcggtctca gaca                                                24
```